US007041492B2

(12) United States Patent
Oka et al.

(10) Patent No.: US 7,041,492 B2
(45) Date of Patent: May 9, 2006

(54) EXTRACELLULAR RECORDING ELECTRODE

(75) Inventors: Hiroaki Oka, Hirakata (JP); Tetsuo Yukimasa, Hirakata (JP); Ryuta Ogawa, Moriguchi (JP); Hirokazu Sugihara, Katano (JP); Katsuyuki Tsuji, Hirakata (JP); Yukifumi Yoshimoto, Amagasaki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 728 days.

(21) Appl. No.: 10/048,662

(22) PCT Filed: Jun. 20, 2001

(86) PCT No.: PCT/JP01/05289

§ 371 (c)(1),
(2), (4) Date: Feb. 1, 2002

(87) PCT Pub. No.: WO03/001194

PCT Pub. Date: Jan. 3, 2003

(65) Prior Publication Data
US 2003/0111343 A1 Jun. 19, 2003

(51) Int. Cl.
*C12M 1/42* (2006.01)

(52) U.S. Cl. .............................. 435/285.2; 435/287.1; 435/288.3; 204/403.01; 204/403.03; 204/412; 204/403.13

(58) Field of Classification Search ............. 435/285.2, 435/173.4, 173.5, 173.6, 173.7, 287.1, 288.3; 204/403.01, 403.03, 412, 403.13
See application file for complete search history.

(56) References Cited

U.S. PATENT DOCUMENTS

| 5,143,090 A | 9/1992 | Dutcher et al. |
| 5,282,844 A | 2/1994 | Stokes et al. |
| 5,810,725 A | 9/1998 | Sugihara et al. |

FOREIGN PATENT DOCUMENTS

| EP | 0 585 933 A2 | 9/1993 |
| EP | 0 689 051 A2 | 6/1995 |
| EP | 0769308 A1 | 4/1997 |
| JP | 4-204244 | 7/1992 |
| JP | 06-078889 | 3/1994 |
| JP | 06-296595 | 10/1994 |
| JP | 2000-333921 | 12/2000 |
| WO | WO 99/34202 | 7/1999 |

OTHER PUBLICATIONS

Copy of European Search Report dated Feb. 15, 2005.
"Multichannel Cell Membrane Potential Measuring System and its Application to Cortical Development Study", by Sugihara, et al., National Technical Report vol. 42, No. 2, Apr. 1996, pp. 112-119.

(Continued)

*Primary Examiner*—David Redding
(74) *Attorney, Agent, or Firm*—Snell & Wilmer L.L.P.

(57) ABSTRACT

A multiple electrode includes a plurality of micro-electrodes provided on a substrate, and a wiring portion for providing an electrical signal to the micro-electrodes or extracting an electrical signal from the micro-electrodes. Each micro-electrode has porous conductive material on its surface, and the impedance of the micro-electrode is 50 kΩ or less. Preferably, the porous conductive material is gold, and formed by the passage of current at a current density of 1.0 to 5.0 A/dm² for 10 to 360 sec. The multiple electrode may include micro-electrodes provided on a substrate in the form of a matrix, a lead line connected to the micro-electrodes, and an electrical junction connected to an end of the lead line.

18 Claims, 14 Drawing Sheets

EXTRACELLULAR RECORDING ELECTRODE

TECHNICAL FIELD

The present invention relates to a multiple electrode for extracellular recording, which is useful in the field of electro-physiology and is used to measure changes in potential associated with the activity of neurons.

BACKGROUND ART

Recently, the applicability of neurons to electronic devices has been vigorously studied as well as the medical study. An action potential is generated in a neuron which is in an active state. A change in the ion permeability of a neuron leads to changes in intra- and extracellular ion concentrations which are responsible for generation of an action potential. Therefore, if a potential change in association with a change in ion concentration around a neuron is measured, the activity of the neuron can be monitored.

The above-described potential measurement utilizing cell activity is conventionally conducted by placing an electrode of glass or metal (e.g., platinum) for measuring an extracellular potential around a cell with the aid of a micro-manipulator or the like. Alternatively, a similar electrode is inserted into a cell so as to measure the electrical activity of the cell. These conventional techniques have the following disadvantages: skill in electrode preparation is required; the electrode has high impedance and therefore the signal is susceptible to external noise; and cells or tissues are injured if an electrode is inserted into the cell. Therefore, conventional electrodes are not suitable for long-term monitoring.

To avoid such problems, the inventors have developed a multiple electrode including a plurality of micro-electrodes made of a conductive material provided on an insulating substrate, and a lead pattern, on which cells or tissue can be cultured (Japanese Laid-Open Publication No. 6-78889, and Japanese Laid-Open Publication No. 6-296595). With this multiple electrode, the activities of neurons can be monitored without injuring cells or tissue for a long period of time.

In the above-described multiple electrode, an uppermost surface of the electrode contacting cells is plated with porous platinum black using electrolysis (Japanese Laid-Open Publication No. 6-78889), or with gold using deposition (Japanese Laid-Open Publication No. 6-296595). In the case of the platinum black plating, although it is easy to adjust the impedance of the electrode to a practical level, i.e., about 50 k$\Omega$ or less, the strength of the electrode is low and therefore the recyclability of the electrode is low. In the case of gold formed by deposition, the strength is improved, but it is difficult to reduce the impedance to about 50 k$\Omega$ or less.

DISCLOSURE OF THE INVENTION

The present invention is intended to solve the above-described problems. The object of the present invention is to provide an extracellular recording electrode having impedance-frequency characteristics suitable for recording an electrical signal of a cell, which has a low level of impedance, insusceptability to external noise, a high strength, and ease in recycling electrodes.

The inventors have found that in production of an extracellular recording electrode, the current density used in forming a conductive material on an uppermost surface thereof is optimized, thereby obtaining a porous conductive material surface which is rough and therefore has an increased surface area, and that the porous conductive material has preferable characteristics for an extracellular recording electrode. The present invention has been completed based on the above-described findings.

The present invention provides a multiple electrode for measuring electro-physiological characteristics of a cell. The electrode includes a plurality of micro-electrodes provided on a substrate, and a wiring portion for providing an electrical signal to the micro-electrodes or extracting an electrical signal from the micro-electrodes. The micro-electrodes have a porous conductive material on a surface thereof, the conductive material is selected from the group consisting of gold, titanium nitride, silver oxide, and tungsten, and the impedance of each of the micro-electrode is 50 k$\Omega$ or less.

Preferably, the porous conductive material is gold, and is provided by passage of current at a current density of 1.0 to 5.0 A/dm$^2$ for 10 to 360 sec.

The present invention also provides a multiple electrode for measuring electro-physiological characteristics of a cell. The electrode includes a plurality of micro-electrodes provided on a substrate, and a wiring portion for providing an electrical signal to the micro-electrodes or extracting an electrical signal from the micro-electrodes. The surface area of the micro-electrode calculated from an electrostatic capacity of an equivalent circuit having substantially the same impedance as that of the micro-electrode, is greater than or equal to at least 10 times and less than 200 times the projection area of the micro-electrode, and the impedance of each of the micro-electrode is 50 k$\Omega$ or less.

The term "projection area of a micro-electrode" as used herein refers to the entire area of an uppermost surface of a micro-electrode before a conductive material is provided.

Preferably, a surface area of the micro-electrode measured by a gas adsorption method is less than or equal to 5×10$^5$ times the projection area of the micro-electrode.

In one embodiment of this invention, the micro-electrodes are arranged on the substrate in a form of a matrix, the wiring portion includes a lead line connected to the micro-electrode and an electrical junction connected to an end of the lead line, and at least a surface of the lead line is covered with an insulating layer.

In one embodiment of this invention, the porous conductive material may be provided by etching, such as RIE (reactive ion etching) and ICPRIE (inductively coupled plasma RIE).

The present invention also provides an integrated cell installer including the above-described multiple electrode. The integrated cell installer has a cell installing region for placing a cell or tissue on the substrate of the multiple electrode.

The present invention also provides a cellular potential measuring apparatus including the above-described integrated cell installer, an output signal processor connected to the micro-electrodes for processing an output signal due to an electro-physiological activity of a cell or tissue, and a stimulus signal provider for optionally providing an electrical stimulus to the cell or tissue.

The present invention also provides a cellular potential measuring system including the above-described cellular potential measuring apparatus, an optical monitoring apparatus for optically monitoring a cell or tissue, and/or a cell culture apparatus for controlling the culture environment of the cell or tissue.

BEST MODE FOR CARRYING OUT THE INVENTION

Figure 1A:
FIG. 1a is a photomicrograph showing a gold plating formed by electrolysis on a surface of a micro-electrode at a current density of 1.0 A/dm$^2$ in a comparative example where a magnification is 2500. The scale bar in the figure is 50 µm.

Hereinafter, the present invention will be described in more detail.

(Production of Porous Conductive Material for Micro-electrode)

A multiple electrode for extracellular recording according to the present invention includes a plurality of micro-electrodes provided on an insulating substrate. Cells are placed on the micro-electrodes to measure the electrical activity of the cells.

The multiple electrode of the present invention particularly includes a porous conductive material on an uppermost surface of the micro-electrode. The impedance of this micro-electrode is 50 kΩ or less. The impedance of the micro-electrode is preferably 35 kΩ or less, more preferably 25 kΩ or less, and even more preferably 10 kΩ or less. An impedance as used herein is defined as a value which is measured at a frequency of 1 kHz and at an interterminal voltage of 50 mV. The lower limit value of the impedance in the present invention is not particularly limited, but is preferably as low as possible in accordance with the teachings of the present invention.

It is believed that such a low impedance is attributed to a porous structure of a conductive material provided on the electrode. The porosity as used herein refers to the state of a conductive material surface being rough or having minute protrusions and depressions. When magnified and observed by an optical microscope, the porous conductive material surface of the present invention appears to be a dense agglutination of about 0.01–25 µm-diameter small particles. When the uppermost surface of the electrode has such a porous structure, the surface area is significantly increased. As a result, a low level of impedance can be achieved which cannot be otherwise obtained in the case of a smooth gold surface which is provided by conventional deposition.

As described above, the porous structure of the uppermost surface of the electrode can be defined by the surface area of the uppermost surface of the electrode. The surface area of the uppermost surface of the electrode may be defined with a BET method using gas absorption which is well known to those skilled in the art, for example. Alternatively, the impedance may be calculated based on the electrostatic capacity of an equivalent circuit of an electric circuit representing a model of an interface between a micro-electrode and a solution.

The porous conductive material of the present invention is representatively produced by electrolytic plating under over-current density. The over-current density preferably refers to a current density in the range of 1.2 A/dm$^2$, more preferably 1.0 to 5.0 A/dm$^2$, and most preferably 1.4 to 2.1 A/dm$^2$. This is contrast to typical industrial electrolytic plating for a conductive material where the current density is about 1.0 A/dm$^2$ or less. Note that even when a current density of more than 3.0 A/dm$^2$ is used, the porous conductive material plating is possible. If a current density is excessively large, the surface is extremely rough so that it is difficult to maintain an intended shape (e.g., square) of a micro-electrode. In the present invention, conductive material plating can be produced by the passage of current for representatively 10–360 seconds, preferably 30–240 seconds, under over-current density. If the passage time of the current is excessively short, a conductive material plating may not be sufficiently formed on a micro-electrode. If the passage time of the current is excessively long, the growth of a conductive material on a micro-electrode is not even, so that some portions of the conductive material plating is rapidly grown while others are slowly grown and the shape of the electrode is likely to deviate from a square.

The above-described conditions for electrolytic plating are only for illustrative purposes, and may be optionally modified within a range in which the above-described low impedance can be achieved, depending on the limitations of the electrolytic plating apparatus used or requirements of operational procedures.

Alternatively, the porous conductive material of the present invention can be obtained by etching. For example, chemical etching using an oxidizing agent and a solubilizing agent, electrochemical etching in which electrolysis is conducted using direct or alternating current in an electrolyte solution containing acid as a major component, or the like can be employed, whereby the surface area can be increased.

The uppermost surface of the micro-electrode of the present invention has the above-described porous structure. Further, a material for the uppermost surface is, for example, gold, whereby a high strength as well as low impedance characteristics can be achieved. Therefore, the recycling efficiency of the micro-electrode is high, resulting in high cost performance. This is contrast to an electrolytic plating of platinum black heavily used in conventional electrodes which has a low level of impedance, but a significantly low level of strength, so that it is not resistant to repetitions of recycling. Specifically, the rate of increase in the impedance of the electrode of the present invention with respect to the original impedance after 20 cycles is representatively 30% or less, preferably 20% or less, and more preferably 15% or less, when a lifetime test is conducted under substantially the same conditions as those in Example 5 described later.

The above-described porous conductive material is provided on the uppermost surface of the micro-electrode of the present invention. An underlying electrode material for the porous conductive material may be any material which can be sufficiently adhered to the porous conductive material. Examples of an underlying electrode material for the porous conductive material include, but are not limited to, preferably nickel by electroless or electrolytic plating, gold by commonly used electroless plating, and the like. The thickness of these underlying layers is not particularly limited. For example, the thickness of the nickel plating is about 3000 to 7000 angstroms. Electroless gold plating having a thickness of about 300 to 700 angstroms may be provided on the nickel plating.

In the multiple electrode of the present invention, representatively, a plurality of micro-electrodes are provided on a substrate in such a manner as to be placed at intersections of a grating in the form of a matrix. In this arrangement, a plurality of electrodes can be equally spaced. Therefore, the cell bodies of adjacent neurons can be placed on adjacent electrodes to detect transfer of an electrical signal between the cell bodies.

Each micro-electrode is externally provided with an electrical signal. Alternatively, a wiring portion for extracting an electrical signal from each micro-electrode to the outside is connected to each electrode. Representatively, the wiring portion includes a lead line which is connected to each micro-electrode and drawn from the electrode towards the periphery of the substrate. The wiring portion may further include an electrical junction connected to an end of the lead line which is typically located at the periphery of the substrate. An example of a material for the wiring portion preferably includes indium tin oxide (ITO). Note that the above-described impedance is an overall characteristic value of the micro-electrode and the wiring portion. In fact, the impedance value of the above-described wiring portion is negligible compared to the value defined by the material and dimensions of the uppermost surface of the electrode. Therefore, selection of materials for the underlying layer of the electrode and the wiring portion substantially does not have an influence on the impedance.

Representatively, the surface of a lead line is covered with an insulating layer. The insulating layer may be provided only on the lead line, but preferably on almost the entire upper surface of the substrate except for the micro-electrodes and the vicinity of the electrical junctions. Examples of the insulating layer preferably include acrylic resin or photosensitive polyimide which are easy to process.

(Configuration of Multiple electrode)

For the detailed design of the multiple electrode of the present invention, any structural features of a known multiple electrode (e.g., Japanese Laid-Open Publication No. 6-78889) can be used as long as the formation and function of the above-described porous conductive material are not interfered with. Hereinafter, a configuration of a representative example of the multiple electrode will be shown. Embodiments as described herein may be optionally modified by taking into consideration various factors, such as the characteristics of neurons to be measured, the nature of data to be measured, and the like.

The substrate included in the multiple electrode is preferably made of a transparent insulating material for the purpose of optical monitoring after cell culture. Examples of such a material include: glass, such as silica glass, lead glass, and borax glass; an inorganic substance, such as quartz; polymethylmethacrylate or a copolymer; and a transparent organic substance, such as polystyrene, and polyethylene terephthalate. An inorganic substance which has mechanical strength and transparency is preferable.

Examples of a material for the electrodes provided on the substrate include indium tin oxide (ITO), tin oxide, Cr, Au, Cu, Ni, Al, and Pt. Among other things, ITO and tin oxide are preferable. ITO having transparency and a high level of conductivity is particularly preferable. The above-described micro-electrode is typically produced by providing the porous conductive material plating on the uppermost surface of a part of the electrode material having a desired position and shape.

Typically, a plurality of micro-electrodes are equally spaced in such a manner that the distances between adjacent electrodes are all equal to each other. The distances between adjacent electrodes may be representatively in the range of from about 10 to about 1000 μm. Representatively, the shape of the electrode is substantially a square or a circle where an edge or a diameter is within the range of from about 20 to about 200 μm. With the above-described settings, if the cell body of a neuron (i.e., a cell body, a dendrite, and an axon) to be measured is located on an electrode, it is highly probable that another cell body, to which a dendrite of the former cell body is connected, is located on an adjacent electrode.

A lead line connected to the micro-electrode may be made of the same electrode material as those described. In this case, ITO is also preferable. Typically, such an electrode material is deposited on a substrate. Thereafter, etching is conducted using a photoresist, thereby forming a desired integrated pattern of a lowermost layer of the micro-electrode and a wiring portion including a lead line. In this case, the thicknesses of the lowermost layer of the micro-electrode and the wiring portion may be about 500 to 5000 angstroms.

The lead line is representatively arranged extending substantially radially from each micro-electrode. In combination with this substantially radial arrangement, a plurality of micro-electrodes are particularly preferably arranged in such a manner that the centers thereof are placed on respective intersections of an 8×8 grating.

An example of a material for an insulating layer covering the lead line includes a transparent resin, such as a polyimide (PI) resin and an epoxy resin. A photosensitive resin, such as negative photosensitive polyimide (NPI), is preferable. For example, when a photosensitive resin is used as the insulating layer material, it is possible to expose only the electrode by forming an opening in the insulating layer portion on the micro-electrode by utilizing a pattern formed by photoetching. As described above, the insulating, layer is provided in such a manner as to cover substantially the entire surface of the insulating substrate except for the vicinity of the electrodes and the electrical junctions with external circuits. This is preferable in terms of production efficiency and the like.

(Apparatus and System for Measuring Cellular Potential)

For the detailed design of various components of a system for effectively utilizing the multiple electrode of the present invention for measuring neurons or the like, any structural features of a known system for measuring a cellular potential (e.g., Japanese Laid-Open Publication No. 8-62209) can be adopted as long as the formation and function of the above-described porous conductive material are not interfered with.

Typically, the multiple electrode of the present invention is additionally provided with a structure for facilitating cell culture to be conducted on the multiple electrode and optionally with another structure for facilitating handling of the multiple electrode. The resultant multiple electrode may be provided as an integrated cell installer.

In order to conduct cell culture on the multiple electrode, representatively, a structural member capable of holding culture medium may be provided via the insulating layer on the substrate which is substantially entirely covered with the insulating layer. For example, a cylinder-like frame made of polystyrene may be fixed on the substrate in such a manner as to surround a plurality of micro-electrodes, thereby obtaining the above-described holding structure. In this case, the inside of the polystyrene frame defines a cell holding region. The porous conductive material plating of the present invention may be formed on the surface of the micro-electrode before or after the provision of the holding structure.

In order to facilitate the handling of the multiple electrode in measuring cells, for example, a printed circuit board may be used. The printed circuit board has a conductor pattern conductively connected to electrical junctions on the multiple electrode, thereby playing a role in extending an electrical connection, which is established from the micro-electrode to the electrical junction, to the outside. A holder having an appropriate shape, such as a two-part split holder which sandwiches the multiple electrode, may be used to reliably fix the printed circuit board with the multiple electrode while keeping the electrical connection therebetween, for example.

The integrated cell installer may be further combined with a stimulus signal provider and an output signal processor, thereby obtaining a cellular potential measuring apparatus for electrically stimulating cells on the multiple electrode, and processing an output signal which is a response to the stimulus.

The stimulus signal provider can apply a stimulus signal to any pair of electrodes out of the plurality of micro-electrodes. When a cell responds to the stimulus signal, another electrode detects a change in evoked potential and outputs an output signal corresponding to the change to a signal processor. The output signal is transferred via an appropriate process to a display apparatus or the like, for example. Note that a spontaneous potential generated in a cell without receiving a stimulus signal may be similarly measured.

The stimulus signal provider and the output signal processor are representatively realized by a single computer having appropriate measurement software. The measurement software provides, on a computer screen, a parameter setting window for setting stimulus conditions and the like, a recording window for recording a potential change detected from a cell and displaying the data via multiple channels in real time, a data analyzing window for analyzing recorded data, and the like. Preferably, a stimulus signal from a computer is transferred via a D/A converter to the multiple electrode, while an output signal from a cell is transferred via an A/D converter to a computer.

A cellular potential measuring apparatus may be further combined with an optical monitoring apparatus and a cell culture apparatus, thereby obtaining a cellular potential measuring system for culturing neurons for a long period of time, and stably and accurately measuring the electrophysiological activities of the neurons. The optical monitoring apparatus may include an inverted microscope, and further an SIT camera for a microscope including a high-definition display and an image file apparatus. As the cell culture apparatus, any apparatus or combination thereof which can control the temperature of the culture atmosphere, the circulation of culture medium, the supply of a gas mixture of air and carbon dioxide, and the like, can be used.

EXAMPLES

Hereinafter, the present invention will be specifically described by way of illustrative examples. The present invention is not limited to these examples.

Example 1

A surface of a planar multiple electrode was coated with electrolytic gold plating under various current densities (a central portion of each electrode having a size of 50×50 μm was positioned at one of intersections of an 8×8 grating. Therefore, the entire surface area of the micro-electrode (projection area) was 50×50×64=160000 μm$^2$).

Specifically, electrolytic gold plating was formed at a current density of 1.0 A/dm$^2$, 1.5 A/dm$^2$, and 2.0 A/dm$^2$. The impedance of the micro-electrode having the gold plating formed at the respective current densities was measured under conditions of a frequency of 1 kHz, an interterminal voltage of 50 mV, and the average of five measurements was calculated. The results are shown in Table 1. As the current density was increased, the average impedance of each of the micro-electrode could be lowered.

TABLE 1

Current Density and Average Impedance

| Current density (A/dm$^2$) | Average impedance (kΩ) |
|---|---|
| 1.0 | 336.39 ± 78.59 |
| 1.5 | 22.07 ± 1.95 |
| 2.0 | 16.56 ± 2.34 |

Figure 1B:
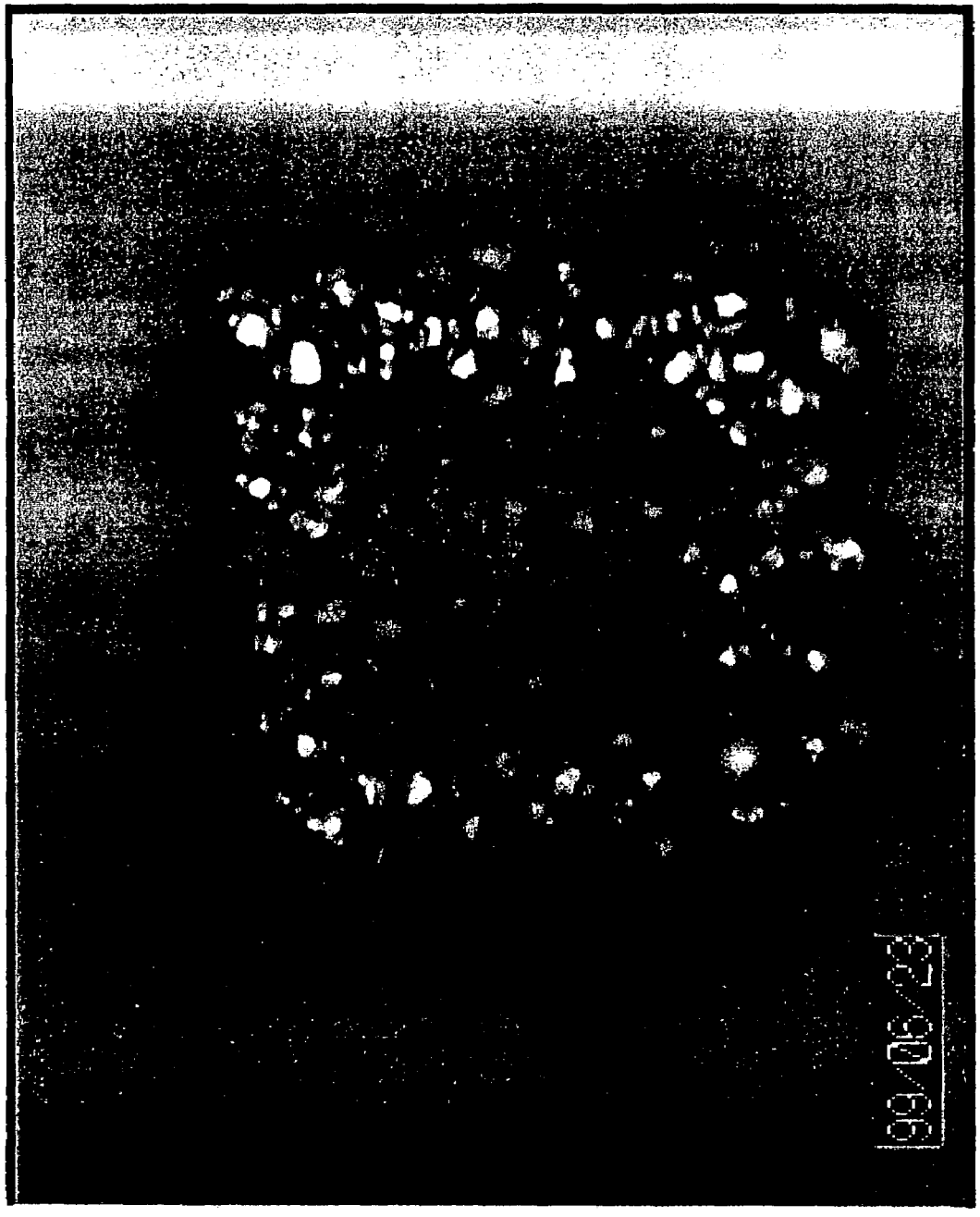
FIG. 1b is a photomicrograph showing a gold plating formed by electrolysis on a surface of a micro-electrode at a current density of 1.5 A/dm$^2$ according to the present invention. The scale bar in the figure is 50 µm.
Figure 1C:
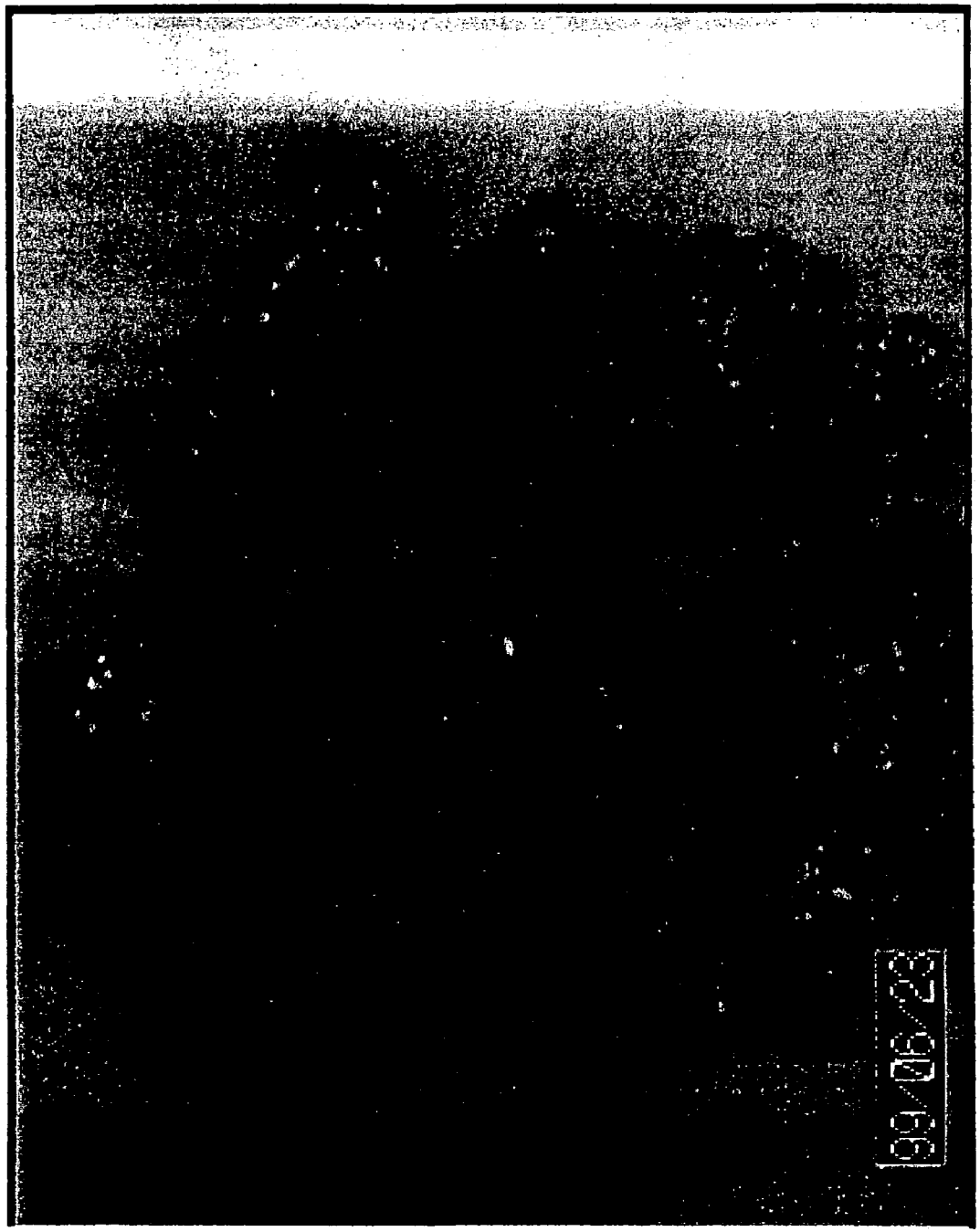
FIG. 1c is a photomicrograph showing a gold plating formed by electrolysis on a surface of a micro-electrode at a current density of 2.0 A/dm$^2$ according to the present invention. The scale bar in the figure is 50 µm.

The gold-plated surface of the micro-electrode was observed with an optical microscope. The photomicrographs are shown in FIGS. 1a to 1c. FIGS. 1a, 1b, and 1c are microphotographs of the plated surfaces which were obtained at a current density of 1.0 A/dm$^2$, 1.5 A/dm$^2$, and 2.0 A/dm$^2$, respectively. In the case of 1.0 A/dm$^2$ current density, a substantially smooth plated surface was obtained. In contrast, as the current density was increased, the porosity of the gold-plated surface was more significant and the area of the electrode surface was increased.

Example 2

The micro-electrode surfaces obtained in Example 1 and slices of the mouse hippocampus (brain) were actually used to measure evoked potentials and noise levels. Hippocampus slices were obtained from a mouse. A five-week-old male c57black6 mouse was anesthetized with Fluothane and decapitated to remove a whole brain. The removed brain was immediately cooled in Ringer's solution on ice. A brain block containing only the hippocampus was dissected. Thereafter, the obtained brain block was cut by a tissue slicer to give a slice having a thickness of 250 μm. The slice was placed and tested on the micro-electrodes.

Figure 2A:
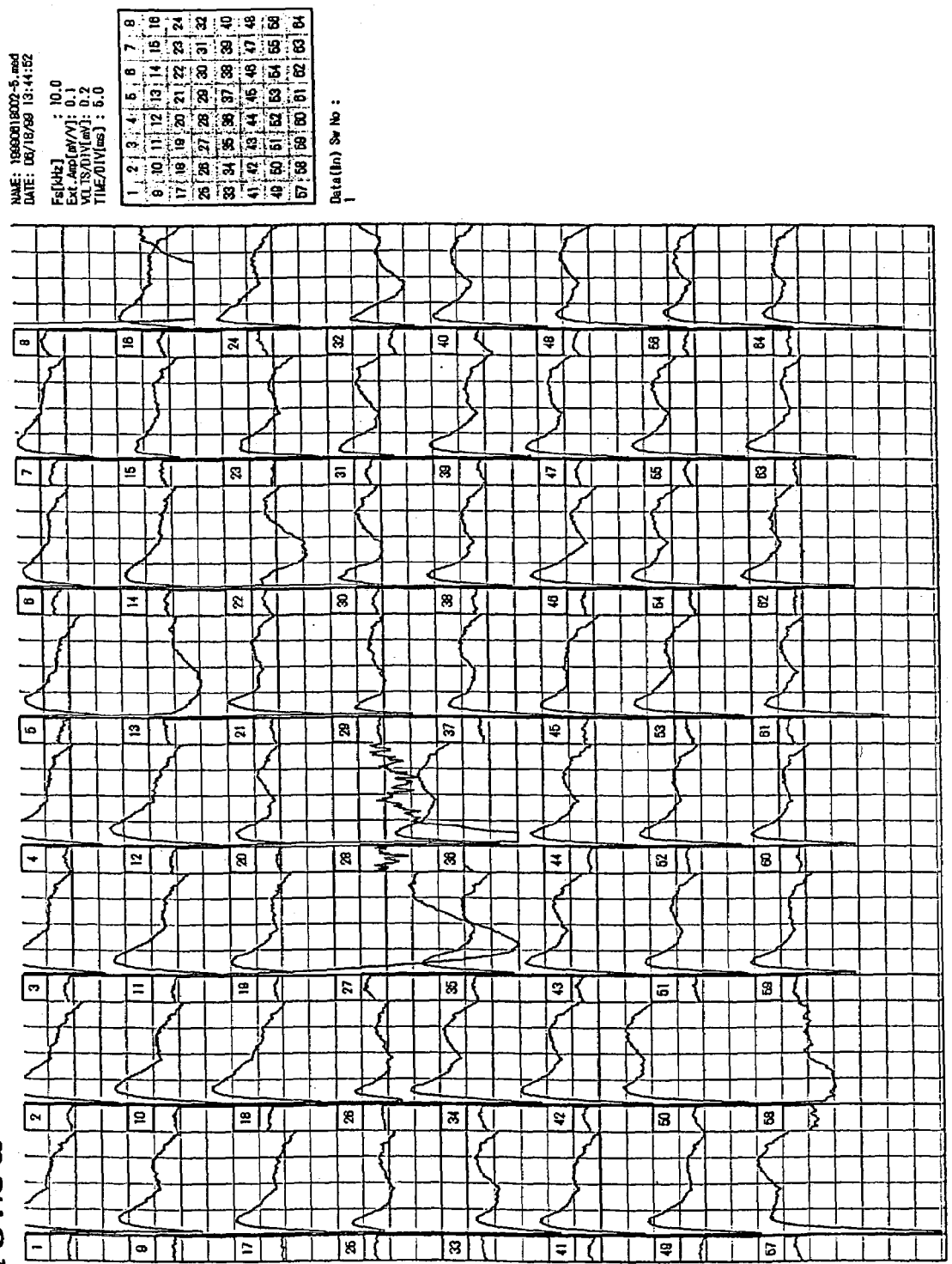
FIG. 2a is a diagram showing a printout of a computer screen displaying 64 channels of potential change responses of cells on gold-plated micro-electrodes obtained by electrolysis at a current density of 1.0 A/dm$^2$ in the comparative example with respect to a constant current stimulus. A stimulus signal is applied to a channel 29.

Evoked potentials and noise levels were measured in the presence of an applied constant current of 10 μA having bipolar pulses (where the pulse width is 100 μsec). Responses of 64 electrodes were measured from 5 msec before stimulation to 45 msec after the stimulation, and were displayed on a computer screen having 64 channels. The results are shown in FIGS. 2a to 2f. FIG. 2a, 2c and 2e show potential change responses (i.e., evoked potentials) of cells on the gold-plated micro-electrode with respect to the above-described constant current stimuli. FIG. 2a shows evoked potentials of the electrode obtained by electrolysis at a current density of 1.0 A/dm$^2$. FIG. 2c shows evoked potentials of the electrode obtained by electrolysis at a current density of 1.5 A/dm$^2$. FIG. 2e shows evoked potentials of the electrode obtained by electrolysis at a current density of 2.0 A/dm$^2$.

Figure 2B:
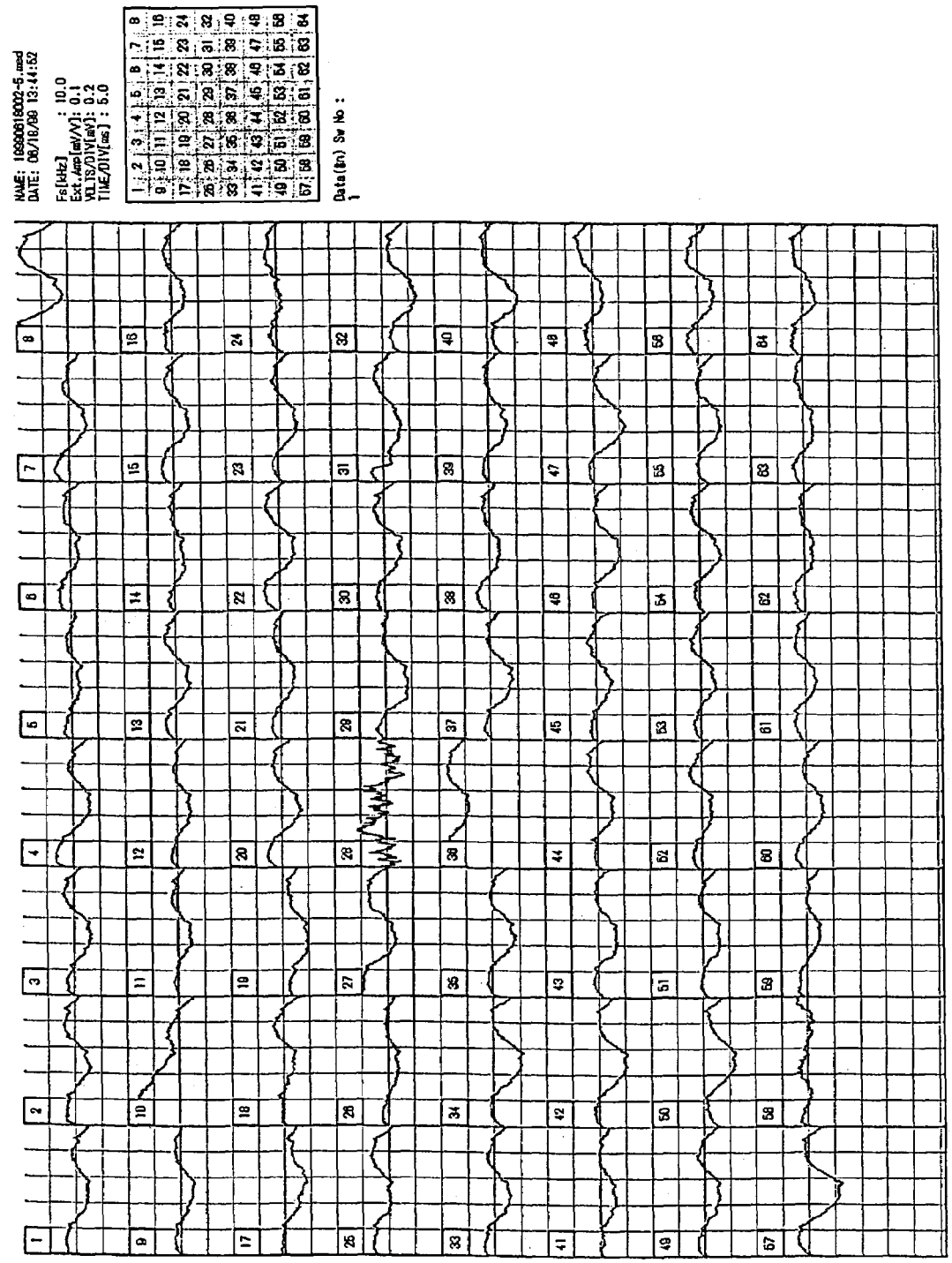
FIG. 2b is a diagram showing a printout of a computer screen displaying 64 channels of noise levels of the gold-plated micro-electrodes shown in FIG. 2a in the absence of cells.
Figure 2C:
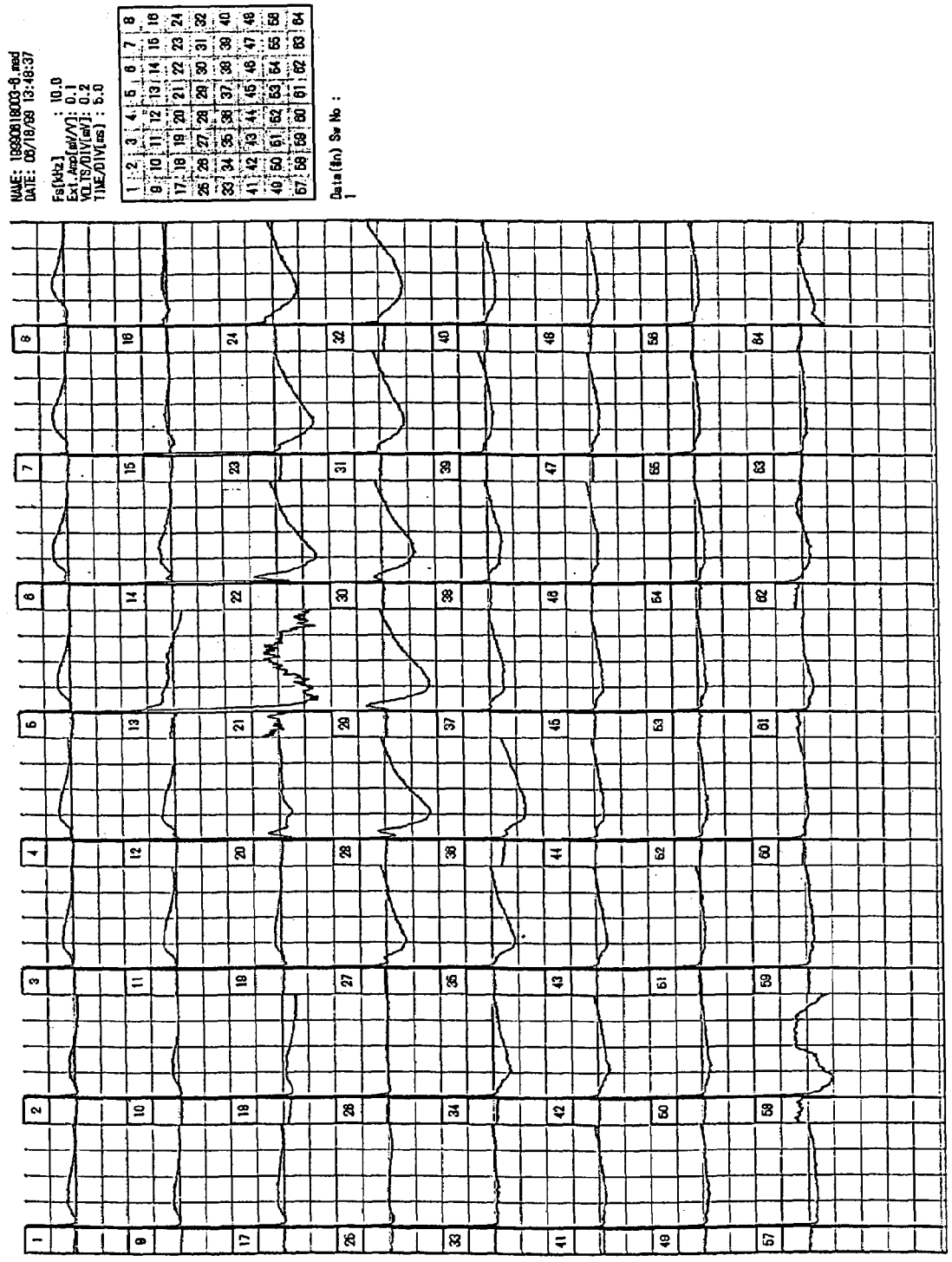
FIG. 2c is a diagram showing a printout of a computer screen displaying 64 channels of potential change responses of cells on gold-plated micro-electrodes obtained by electrolysis at a current density of 1.5 A/dm$^2$ according to the present invention with respect to a constant current stimulus.
Figure 2D:
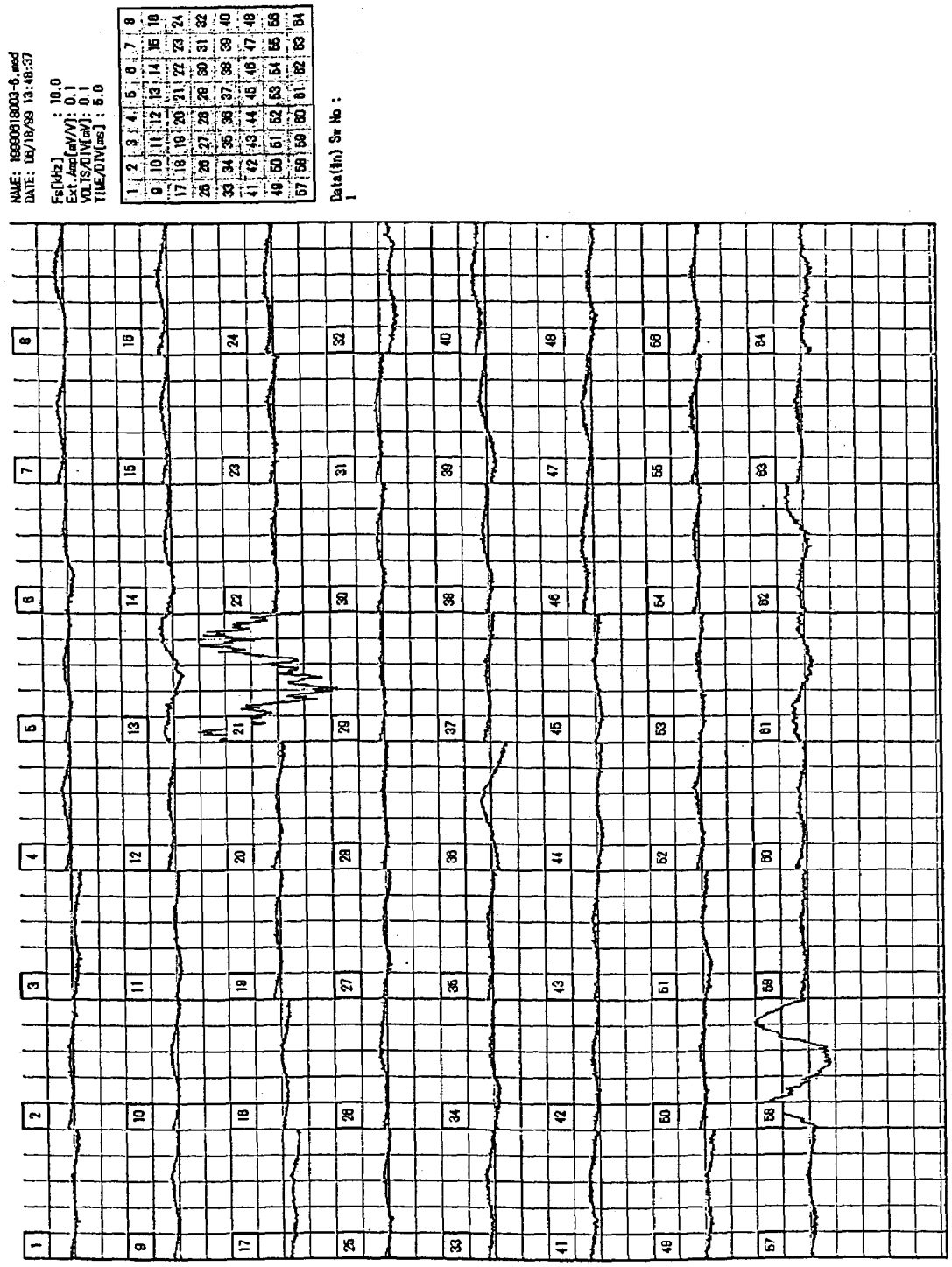
FIG. 2d is a diagram showing a printout of a computer screen displaying 64 channels of noise levels of the gold-plated micro-electrodes shown in FIG. 2c in the absence of cells.
Figure 2E:
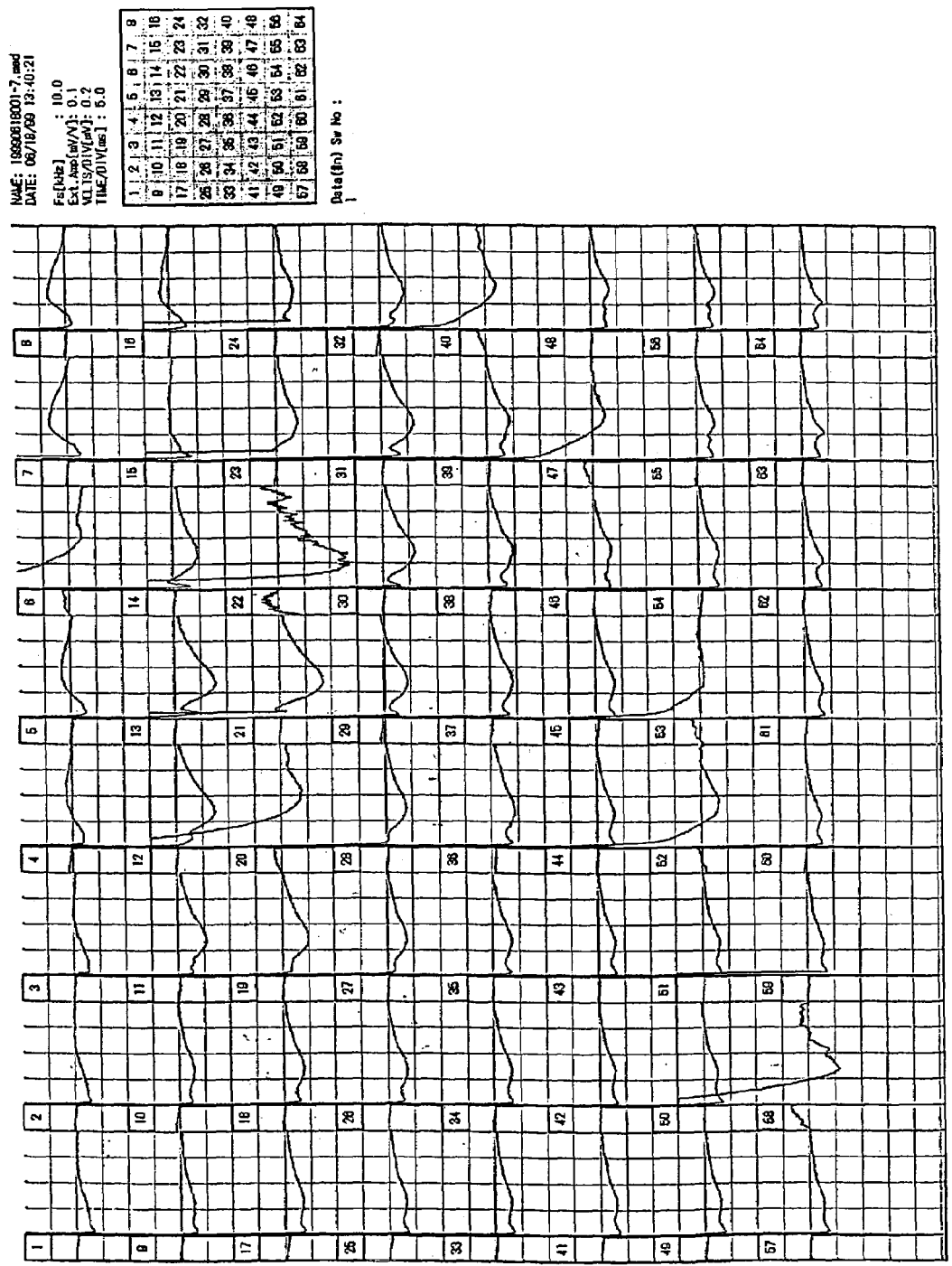
FIG. 2e is a diagram showing a printout of a computer screen displaying 64 channels of potential change responses of cells on gold-plated micro-electrodes obtained by electrolysis at a current density of 2.0 A/dm$^2$ according to the present invention with respect to a constant current stimulus.
Figure 2F:
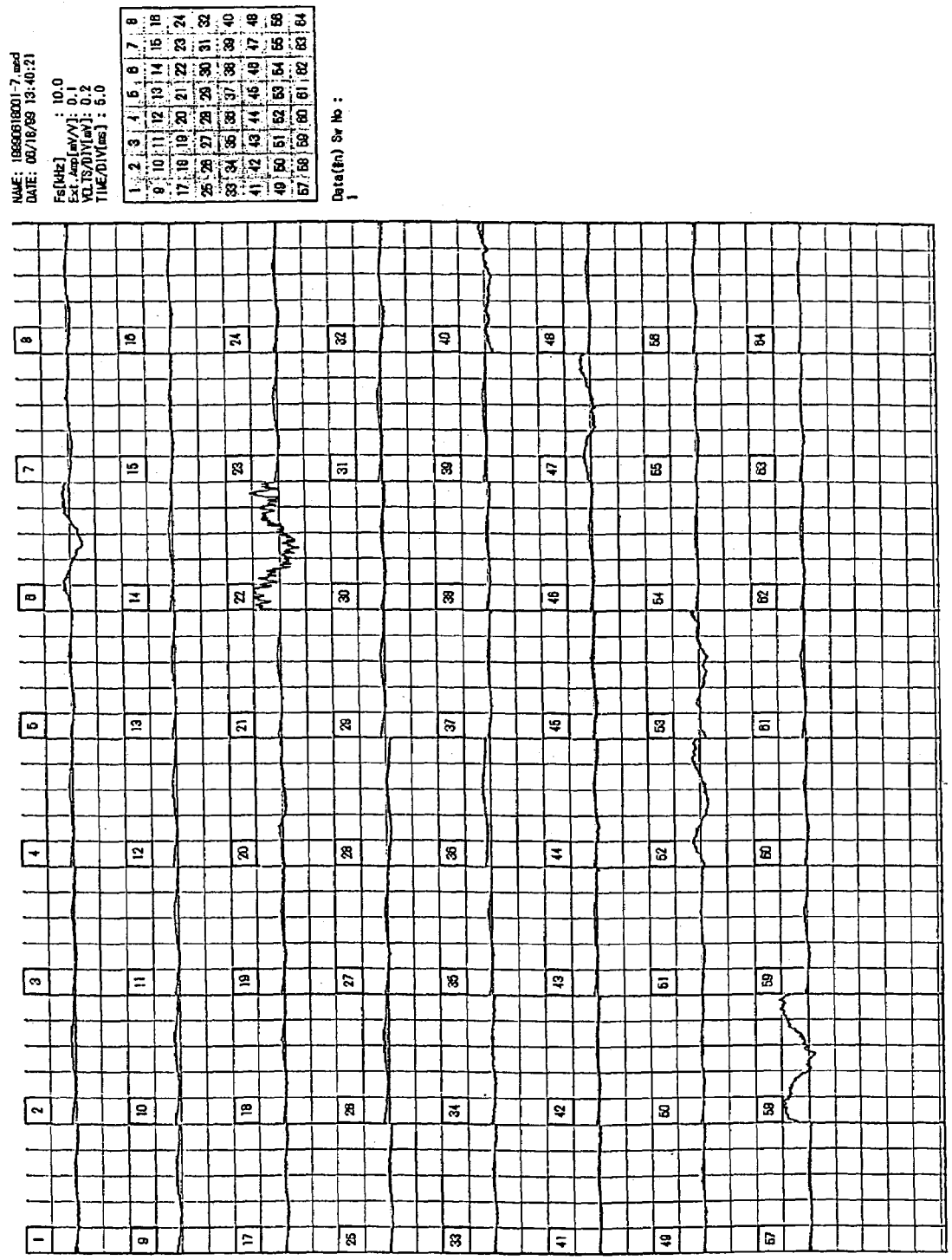
FIG. 2f is a diagram showing a printout of a computer screen displaying 64 channels of noise levels of the gold-plated micro-electrodes shown in FIG. 2e in the absence of cells.

FIGS. 2b, 2d and 2f show noise levels occurred in the respective gold-plated micro-electrodes shown in FIGS. 2a, 2c and 2e.

As can be seen from FIGS. 2a, 2c and 2e, the electrodes having the porous gold plating obtained by a higher level of current density had clear responses to the applied stimulus signals and it is possible to apply a constant current stimulus to the electrodes in an effective manner, as compared to the gold plating (FIG. 2a) obtained by electrolysis at a current density of 1.0 A/dm$^2$ (FIGS. 2c and 2e). Particularly, the micro-electrode having plating obtained at a current density of 1.5 A/dm$^2$ had a low impedance value and a satisfactory surface state.

As to noise level, the plating (FIG. 2f) obtained at a current density of 2.0 A/dm$^2$ had the lowest value, and the plating (FIG. 2d) obtained at a current density of 1.5 A/dm$^2$ had the second lowest value. In contrast, the plating (FIG. 2b) obtained at a current density of 1.0 A/dm$^2$ had a significant level of noise, and it was difficult to measure changes in potential of neurons with high precision.

Example 3

Frequency characteristics of planar micro-electrode surfaces coated with electrolytic gold plating obtained at various current densities were compared with those of a conventional product. Electrodes having porous gold-plated surfaces obtained at a current density of 2.0 A/dm$^2$ and 1.5 A/dm$^2$, respectively, had frequency characteristics similar to that of a conventional electrode having platinum black plating obtained by electrolysis. However, the gold plating obtained at a current density of 1.0 A/dm$^2$ had frequency characteristics significantly inferior to those of the conventional product.

Example 4

A micro-electrode surface area was measured or calculated by the following methods.

1. Measurement by Gas Adsorption Method

The surface area of the micro-electrode having a porous gold-plated surface obtained in Example 1 at a current density of 1.5 A/dm$^2$ was measured with a gas adsorption method using CO gas. As a specimen to be measured, 64 gold-plated micro-electrodes provided on a 1.3 mm×1.3 mm×1.1 mm glass substrate (hereinafter referred to as a gold-plated micro-electrode block) were used. A single micro-electrode is too small to be used as a specimen to be measured with the gas adsorption method. In addition, 64 platinum black-plated micro-electrodes (hereinafter referred to as a platinum black-plated micro-electrode block) provided on a glass substrate as described above but having platinum black plating by a conventional method (electrolytic plating) instead of gold plating, were used as comparative specimens. Note that each of the specimen blocks had a weight of 0.004 g. The results of the measurement are shown in Table 2.

TABLE 2

Results of Measurement of Surface Area of Electrode having Gold-plated Surface

| Specimen | Surface area |
|---|---|
| Gold-plated micro-electrode block | 0.02 m$^2$/g or less |
| Platinum black-plated micro-electrode block (comparative example) | 20.2 m$^2$/g |

The entire surface area of the gold-plated micro-electrode block or the platinum black-plated micro-electrode block is represented by:

$$S'=(S-s)+\alpha s$$

where S' represents the entire surface area of the gold-plated micro-electrode block or the platinum black-plated micro-electrode block (hereinafter referred to as a micro-electrode block); S represents the entire surface area of the micro-electrode block before forming plating on a 1.3 mm×1.3 mm×1.1 mm glass substrate; s represents the surface area of a micro-electrode before plating (projection area), S' represents the entire surface area of the gold-plated micro-electrode block or the platinum black-plated micro-electrode block; as represents an increase in the surface area s of a micro-electrode by plating by a factor of α; and S-s, i.e., the surface area of the micro-electrode block excluding the micro-electrode is not changed and only the surface area of the micro-electrode is increased by plating. The value of α is calculated by:

$$\alpha = (S'-S)/s + 1.$$

In this case, the value of S is the surface area of a 1.3 mm×1.3 mm×1.1 mm rectangular parallelepiped, i.e., 7.41 mm². The value of s (projection area) is the surface area of the 64 electrodes each having a size of 50 m×50 μm, i.e., 0.16 mm². Therefore, according to the measurement result of S' shown in Table 2, the value of α of the platinum black-plated micro-electrode is calculated, to be 504955. Note that the value of α (an increase in the surface area) of the gold-plated electrode is below the detection limit of the gas adsorption method, and is estimated to be less than 455.

Figure 3:
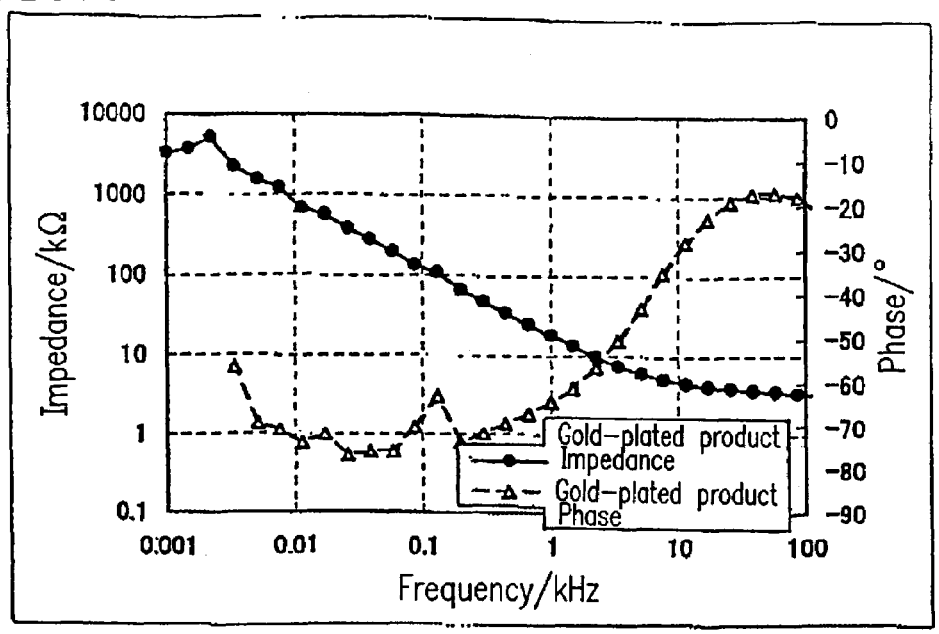
FIG. 3 is a diagram showing an impedance characteristic of the micro-electrode of the present invention.

2. Calculation of Surface Area of Micro-electrode 2. 1. Impedance characteristics of Gold-plated Electrode The impedance of the micro-electrode of Example 1 having a porous gold-plated surface obtained at a current density of 1.5 A/dm² was measured by continuously changing frequency from 1 Hz to 100 kHz. In this measurement, a 0.3 mmφ platinum line was used as a counter electrode and the measurement was conducted in 1.4 wt % NaCl aqueous solution. The bias voltage was zero volts, and the amplitude of a measuring voltage was 50 mV. The results are shown in FIG. 3. FIG. 3 is a Bode diagram, well-known to those skilled in the art, showing the results of the impedance measurement, where the logarithm of the absolute value of a measured impedance Z (i.e., log|Z|) and the phase angle (θ) are plotted with respect to the logarithm of frequency f. Based on the Bode diagram, the measurement system is represented by an, equivalent circuit, thereby quantifying the surface area of the micro-electrode.

Figure 4A:
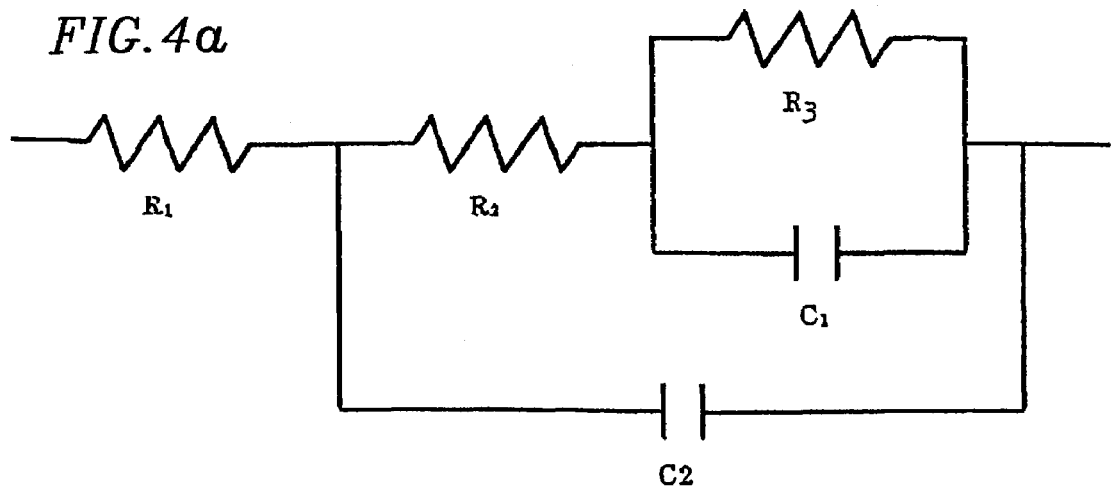
FIG. 4a is a diagram showing an equivalent circuit of the micro-electrode of the present invention.

The measurement system including the micro-electrode can be estimated to be equivalent to a circuit actually including a capacitance generated between the ITO circuit pattern portion and a solution, a resistance generated on a micro-electrode interface, and the like, in addition to the resistance of the solution, the resistance of the ITO circuit pattern, a capacitance of an electric double layer in the micro-electrode surface, and the like, which are complicatedly connected in series and parallel. For example, FIG. 4a shows an equivalent circuit of the measurement system including micro-electrode. The synthetic impedance Z of the entire equivalent circuit shown in FIG. 4a can be represented by:

$$Z = R_1 + \frac{(R_2+R_3)(1-\omega^2 R_2 R_3 C_1 C_2) + \omega^2 R_2 R_3 C_1 \{R_3 C_1 + (R_2+R_3)C_2\}}{(1-\omega^2 R_2 R_3 C_1 C_2)^2 + [\omega\{R_3 C_1 + (R_2+R_3)C_2\}]^2}$$

$$- j\omega \frac{(R_2+R_3)\{R_3 C_1 + (R_2+R_3)C_2\} - R_2 R_3 C_1(1-\omega^2 R_2 R_3 C_1 C_2)}{(1-\omega^2 R_2 R_3 C_1 C_2)^2 + [\omega\{R_3 C_1 + (R_2+R_3)C_2\}]^2}$$

[I]

where $R_1$ represents the resistance of the ITO circuit pattern portion (which does not contact the solution); $R_2$ represents the resistance of the ITO circuit pattern portion and the resistance of the solution; $R_3$ represents the resistance of the micro-electrode surface; $C_1$ represents the capacitance of the electric double layer of the micro-electrode surface; $C_2$ represents the capacitance generated between the ITO circuit pattern portion and the solution via an insulating film; and $\omega = 2\pi f$ ($\omega$: angular frequency and f: frequency). The absolute value |Z| of the above-described synthetic impedance and the phase θ are represented by $|Z| (Z_{Re}^2 + Z_{Im}^2)^{1/2}$ and $\theta = \tan^{-1}(-Z_{Im}/Z_{Re})$ (where $Z_{Re}$ is the real part of Z and $Z_{Im}$ is the imaginary part of Z), respectively.

Figure 5:
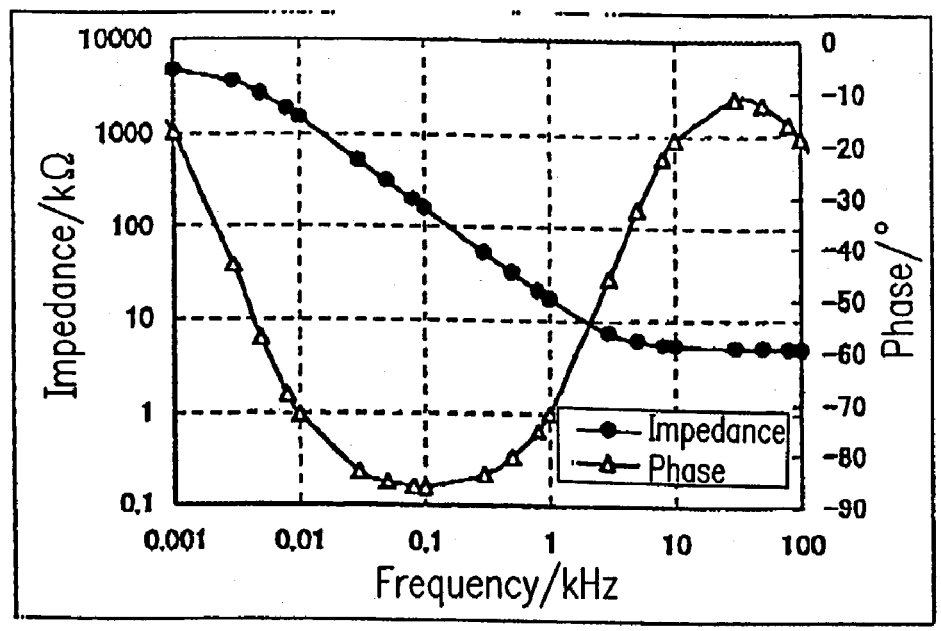
FIG. 5 is a diagram showing an impedance characteristic of an equivalent circuit of the micro-electrode of the present invention.

Here, the equivalent circuit shown in FIG. 4a was simulated by calculating the synthetic impedance of the equivalent circuit by changing $R_1$, $R_2$, $C_1$ and $C_2$ to select a combination of $R_1$, $R_2$, $R_3$, $C_1$ and $C_2$ which provide a Bode diagram most approximate to the Bode diagram shown in FIG. 3. FIG. 5 is a Bode diagram where $R_1$=200 Ω, $R_2$=5 kΩ, $R_3$=5 MΩ, $C_1$=0.01 μF and $C_2$=100 pF. It is apparent that the results shown in FIG. 5 are in agreement with the results of the actual measurement shown in FIG. 3 to an excellent extent.

Here, in the measurement system including the micro-electrode, $R_3 \gg R_1$, $R_3 \gg R_2$ and $C_2 \ll C_1$. Therefore, if it is assumed that $R_3 \rightarrow \infty$ and $C_2 \rightarrow 0$, the above-described expression [I] can be approximated by:

$$\lim_{R_3 \to \infty} \lim_{C_2 \to 0} Z = R_1 + R_2 - j\frac{1}{\omega C_1} = R_1 + R_2 + \frac{1}{j\omega C_1} \quad [II]$$

Figure 4B:
FIG. 4b is a diagram showing an equivalent circuit of the micro-electrode of the present invention.

If $R_1 + R_2 = R$ and $C_1 = C$, the measurement system including the micro-electrode can be approximated by a simple circuit shown in FIG. 4b. Hereinafter, analysis was further conducted using the equivalent circuit shown in FIG. 4b.

The synthetic impedance Z of the entire equivalent circuit shown in FIG. 4b is represented by $Z = R + (j\omega C)^{-1}$ where R represents the resistance of a circuit pattern; C represents the resistance of the electric double layer of the micro-electrode surface; and $\omega = 2\pi f$ ($\omega$ represents angular frequency and f represents frequency). The absolute value |Z| of the above-described synthetic impedance and the phase θ are represented by $|Z| = (R^2 + (1/\omega C)^2)^{1/2}$ and $\theta = \tan^{-1}(-\omega C/R)$, respectively.

Figure 6:
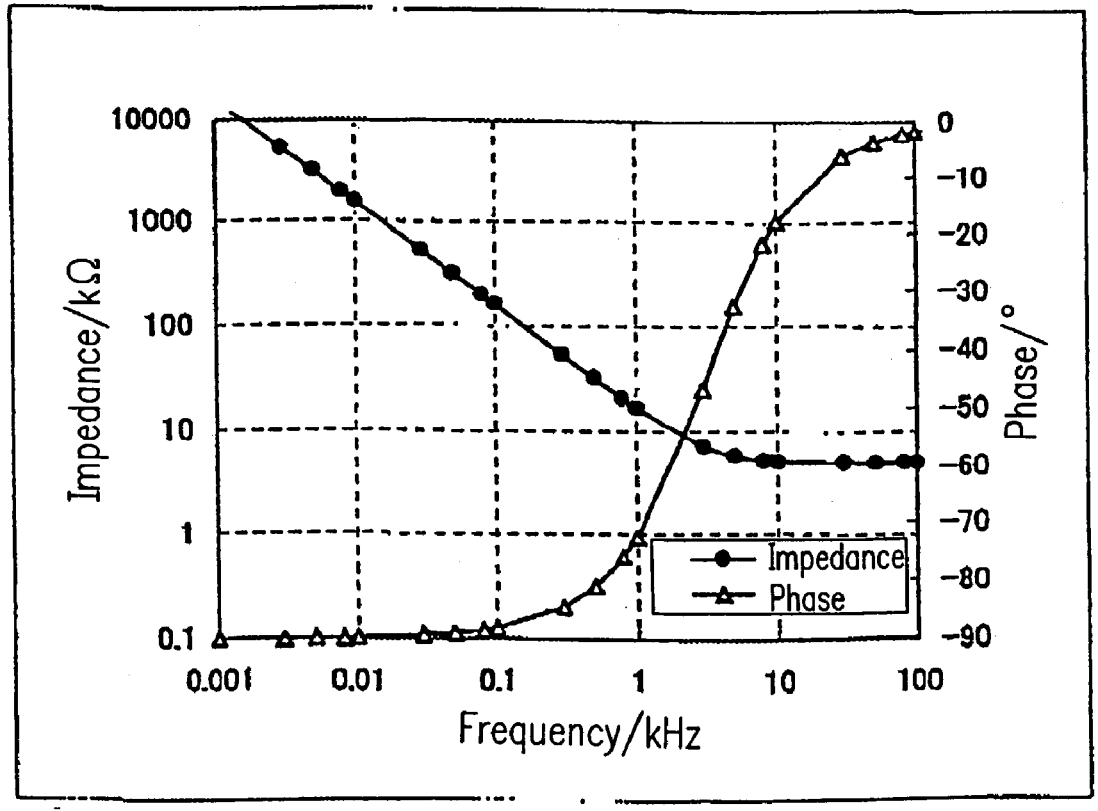
FIG. 6 is a diagram showing an impedance characteristic of an equivalent circuit of the micro-electrode of the present invention.

The equivalent circuit shown in FIG. 4b was simulated by calculating the synthetic impedance of the equivalent circuit by changing the values of R and C to select a combination of R and C which provides a Bode diagram which is most approximate to the Bode diagram shown in FIG. 3. FIG. 6 is a Bode diagram where R=5 kΩ and C=0.01 μF. It is apparent that the results shown in FIG. 6 are in agreement with the results of the actual measurement shown in FIG. 3 to an excellent extent.

Figure 7:
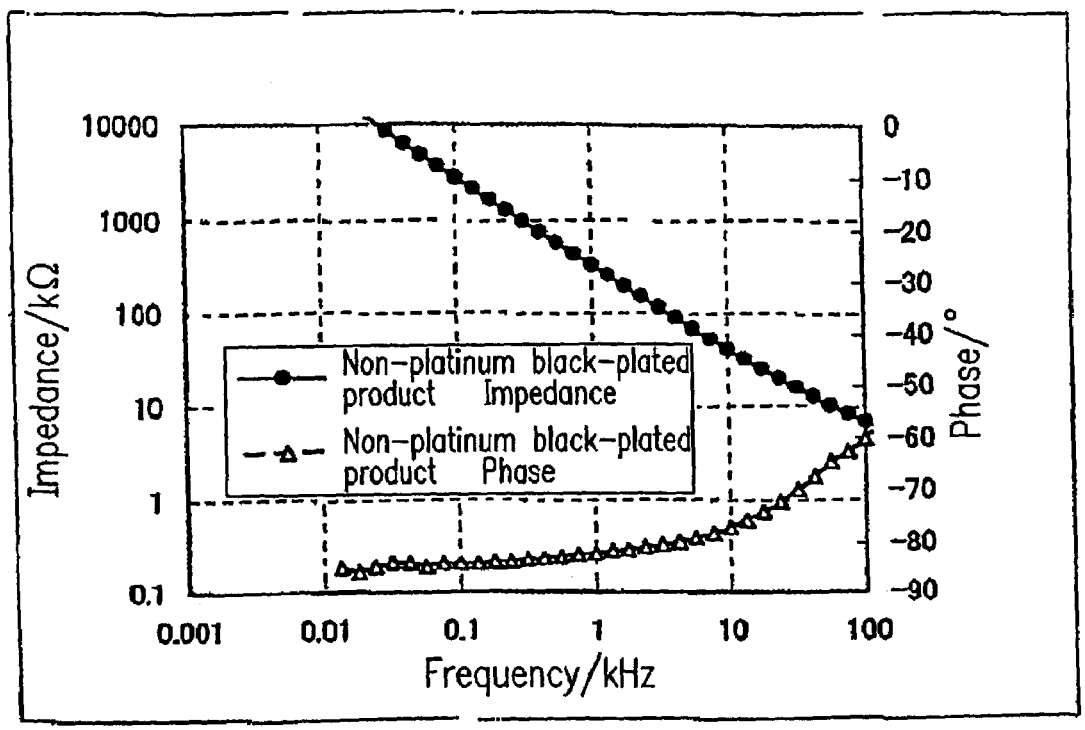
FIG. 7 is a diagram showing an impedance characteristic of a micro-electrode of a comparative example.

Next, FIG. 7 is a graph showing the actually measured values of the impedance of a micro-electrode used as a control, which does not have a gold-plated surface. The measurement conditions are the same as used in measuring the impedance of the multiple electrode having the above-described gold-plated surface (FIG. 3).

Figure 8:
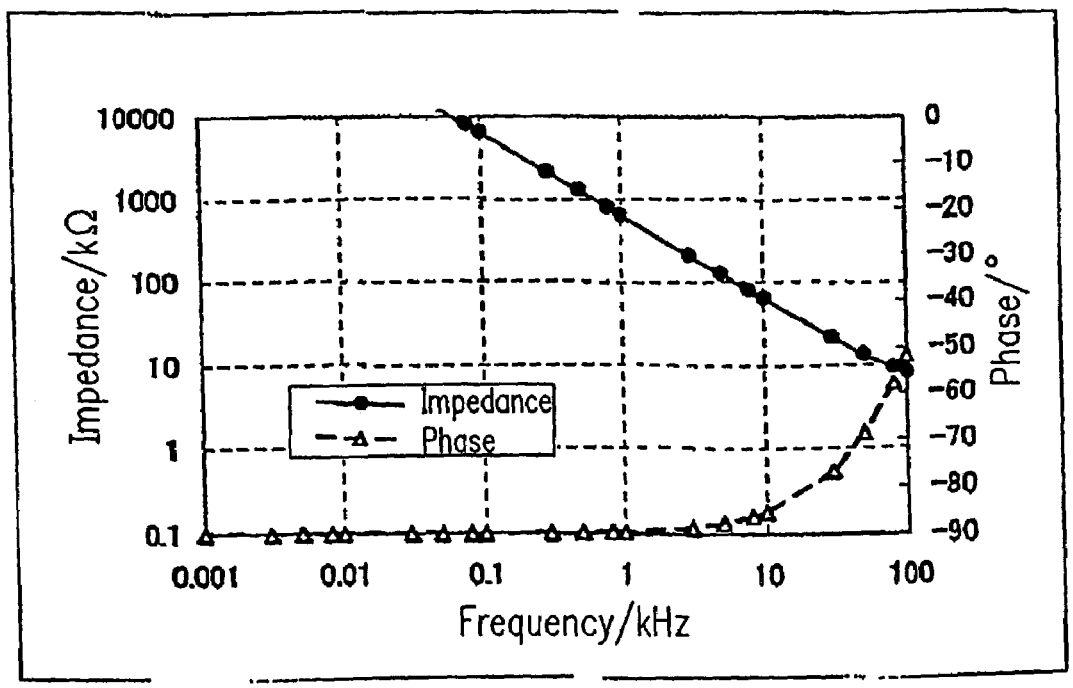
FIG. 8 is a diagram showing an impedance characteristic of an equivalent circuit of a micro-electrode of a comparative example.

Next, FIG. 8 shows the results of the synthetic impedance of the equivalent circuit obtained by simulation of the equivalent circuit shown in FIG. 4b where R=5 kΩ and C=250 pF. It is apparent that the results shown in FIG. 8 are in agreement with the results of the actual measurement shown in FIG. 7 to an excellent extent.

Here, it is assumed that the capacitance of the electric double layer of a micro-electrode having a gold-plated surface is represented by $C_A$ and the capacitance of the electric double layer of the micro-electrode before gold plating treatment is represented by $C_B$. According to the above-described simulation results, the electrostatic capacities $C_A$ and $C_B$ of the micro-electrode are 0.01 µF and 250 pF, respectively, whereby a relationship $C_A=40C_B$ is obtained. Here, generally, electrostatic capacity $C_{ap}$ is represented by $C_{ap}=\epsilon_0\epsilon_r S/d$ ($\epsilon_0$: the dielectric constant of a vacuum; $\epsilon_r$: the relative dielectric constant of a dielectric material; S: the surface area of an electrode; and d : the thickness of the dielectric material). The value of electrostatic capacity $C_{ap}$ is proportional to the surface area of the electrode. Therefore, the above-described relationship indicates that the surface area of a micro-electrode having a gold-plated surface is increased by a factor of 40 by the provision of the gold plating.

Figure 9:
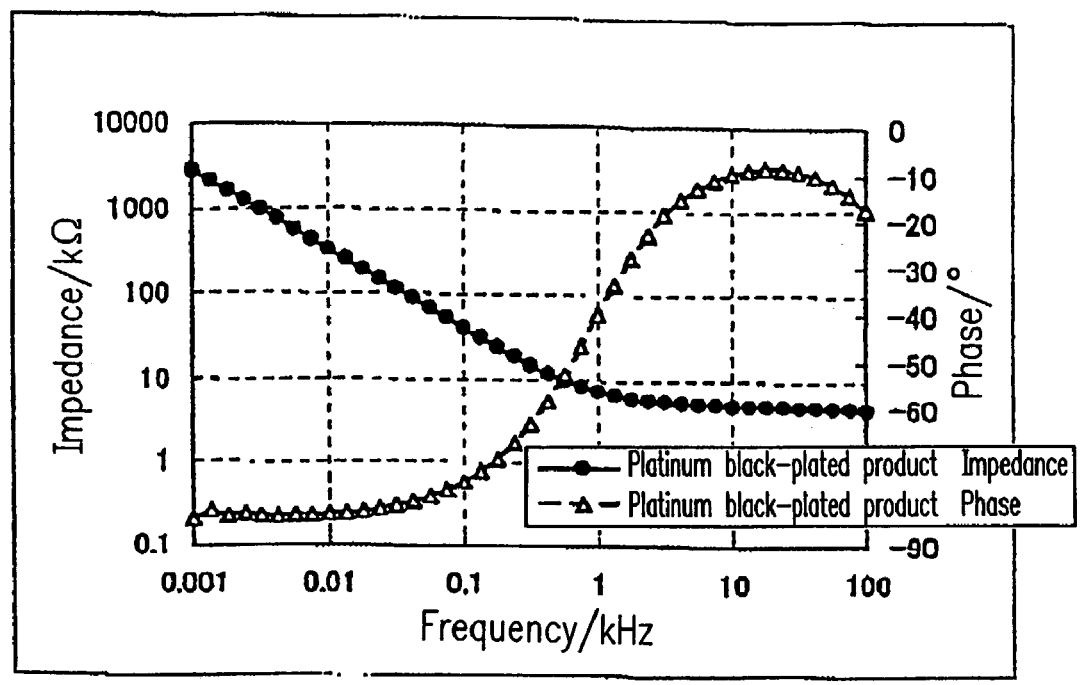
FIG. 9 is a diagram showing an impedance characteristic of a micro-electrode of a comparative example.
Figure 10:
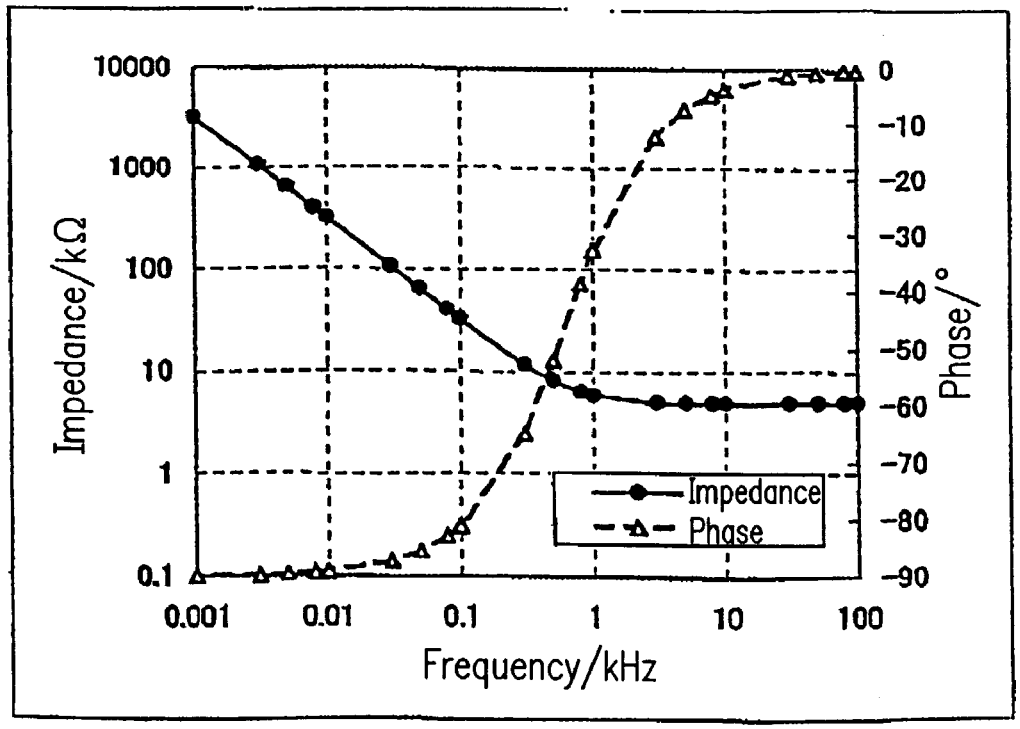
FIG. 10 is a diagram showing an impedance characteristic of an equivalent circuit of a micro-electrode of a comparative example.

FIG. 9 is a graph showing the actually measured values of the impedance of a micro-electrode having a platinum black-plated surface in a manner similar to a micro-electrode having a gold-plated surface. The measurement conditions are the same as used in measuring the impedance of a micro-electrode having a gold-plated surface (FIG. 3). Next, FIG. 10 shows the result of the synthetic impedance of the equivalent circuit shown in FIG. 4b obtained by simulation where R=5 kΩ and C=0.05 µF. It is apparent that the results shown in FIG. 10 are in agreement with the results of the actual measurement shown in FIG. 9 to an excellent extent.

Similarly, it is assumed here that the capacitance of the electric double layer of a micro-electrode having a gold-plated surface is represented by $C_A$ and the capacitance of the electric double layer of the micro-electrode before gold plating treatment is represented by $C_B$. According to the above-described simulation results, the electrostatic capacities $C_A$ and $C_B$ of the micro-electrodes are 0.01 µF and 0.05 µF, respectively, whereby a relationship $C_A=200C_B$ is obtained. This relationship indicates that the surface area of a micro-electrode having a gold-plated surface is increased by a factor of 200 by the provision of the gold plating.

According to this simulation, in order to obtain an impedance of 50 kΩ or less, which is the limit of the impedance of a micro-electrode, the surface area needs to be increased by a factor of 10 or more using gold plating, compared to the projection area.

Example 5

Figure 11:
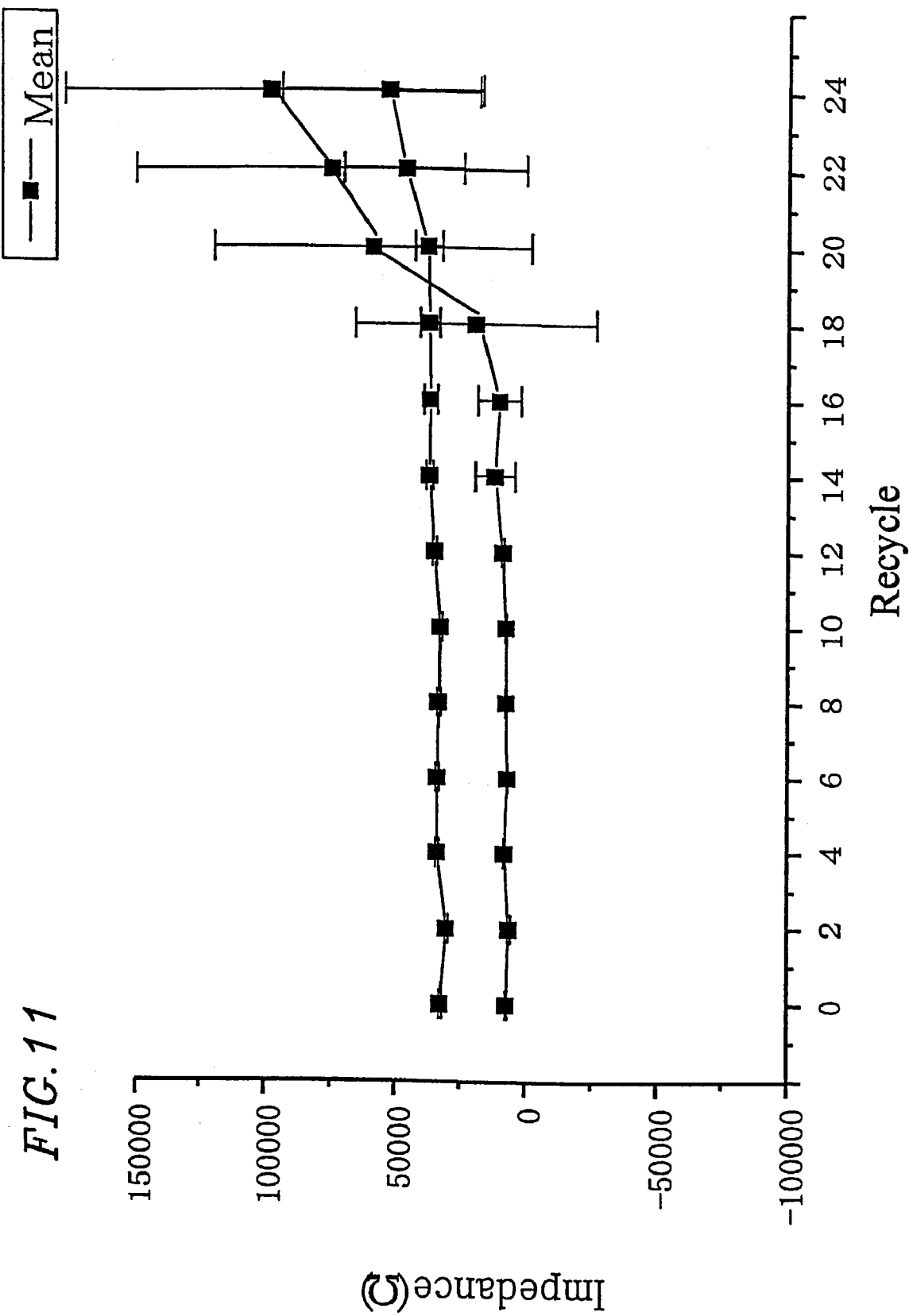
FIG. 11 is a graph showing a result of a lifetime test in which an electrolytic gold-plated micro-electrode of the present invention is compared with a conventional product in terms of reusability.

A planar multiple electrode having porous gold plating obtained by electrolysis at a current density of 1.5 A/dm² was subjected to a lifetime test in comparison with a conventional electrode (platinum black plating). In the lifetime test, an experiment similar to a typical acute experiment was repeated. Specifically, an experiment as described in Example 2 was repeated. After the end of each experiment, the electrode was treated with collagenase (20 u/ml) overnight and a cell slice specimen was peeled off, followed by washing with distilled water. Subsequently, the impedance of the micro-electrode was measured. FIG. 11 is a graph in which the impedance changes after the end of each experiment are plotted. According to the result, an increase and variation in the impedance with an increase in the number of times of use is smaller than that of conventional plating (platinum black plating).

In contrast, the impedance of a conventional product having a platinum black-plated surface by electrolysis was significantly increased after 17 to 18 cycles as shown in FIG. 11. As described above, an electrode having porous gold plating has a higher level of recyclability, and the potential change of the electrode can be stably measured, as compared to conventional products.

Although the present invention is described with reference to the above-described examples, the present invention is not limited to these examples. The present invention may be implemented to modified, improved, and changed embodiments based on the knowledge of those skilled in the art without departing the scope of the present invention.

INDUSTRIAL APPLICABILITY

According to the present invention, a multiple electrode for extracellular recording is provided which has a high strength, is capable of recording the electrical activities of neurons for a long period of time, and is easy to recycle. A plurality of micro-electrodes included in the multiple electrode have a low level of impedance without loss of the strength by utilizing porous gold plating. Therefore, it is easy to apply a constant current stimulus to the multiple electrode, and the multiple electrode is preferably suited to monitor a response of a cultured cell to an electrical stimulus.

What is claimed is:

1. A multiple electrode for measuring electro-physiological characteristics of a cell, the electrode comprising:
   a plurality of micro-electrodes provided on a substrate; and a wiring portion for providing an electrical signal to each of the micro-electrodes or extracting an electrical signal from each of the micro-electrodes,
   wherein the micro-electrodes have a porous conductive material on a surface thereof, the conductive material is selected from the group consisting of gold, titanium nitride, silver oxide, and tungsten, and the impedance of each of the micro-electrodes is 50 kΩ or less.

2. A multiple electrode according to claim 1, wherein the porous conductive material is gold, and is provided by passage of current at a current density of 1.0 to 5.0 A/dm² for 10 to 360 sec.

3. A multiple electrode for measuring electro-physiological characteristics of a cell, the electrode comprising:
   a plurality of micro-electrodes provided on a substrate; and a wiring portion for providing an electrical signal to each of the micro-electrodes or extracting an electrical signal from each of the micro-electrodes,
   wherein the surface area of each of the micro-electrodes calculated from an electrostatic capacity of an equivalent circuit having substantially the same impedance as that of each of the micro-electrodes, is greater than or equal to at least 10 times and less than 200 times the projection area of each of the micro-electrode, and the impedance of each of the micro-electrodes is 50 kΩ or less.

4. A multiple electrode according to claim 3, wherein a surface area of the micro-electrodes measured by a gas adsorption method is less than or equal to $5 \times 10^5$ times the projection area of the micro-electrode.

5. A multiple electrode according to any of claims 1, wherein the micro-electrodes are arranged on the substrate in a form of a matrix, the wiring portion includes a lead line connected to each of the micro-electrodes and an electrical junction connected to an end of the lead line, and at least a surface of the lead line is covered with an insulating layer.

6. A multiple electrode according to claim 2, wherein the micro-electrodes are arranged on the substrate in a form of a matrix, the wiring portion includes a lead line connected to each of the micro-electrodes and an electrical junction connected to an end of the lead line, and at least a surface of the lead line is covered with an insulating layer.

7. A multiple electrode according to claim 3, wherein the micro-electrodes are arranged on the substrate in a form of a matrix, the wiring portion includes a lead line connected to each of the micro-electrodes and an electrical junction connected to an end of the lead line, and at least a surface of the lead line is covered with an insulating layer.

8. A multiple electrode according to claim 4, wherein the micro-electrodes are arranged on the substrate in a form of a matrix, the wiring portion includes a lead line connected to each of the micro-electrodes and an electrical junction connected to an end of the lead line, and at least a surface of the lead line is covered with an insulating layer.

9. A multiple electrode according to claim 1, wherein the porous conductive material is provided by etching.

10. A multiple electrode according to claim 3, wherein the porous conductive material is provided by etching.

11. A multiple electrode according to claim 4, wherein the porous conductive material is provided by etching.

12. A multiple electrode according to claim 5, wherein the porous conductive material is provided by etching.

13. An integrated cell installer comprising a multiple electrode according to claim 1, wherein the integrated cell installer has a cell installing region for placing a cell or tissue on the substrate of the multiple electrode.

14. An integrated cell installer comprising a multiple electrode according to claim 2, wherein the integrated cell installer has a cell installing region for placing a cell or tissue on the substrate of the multiple electrode.

15. An integrated cell installer comprising a multiple electrode according to claim 3, wherein the integrated cell installer has a cell installing region for placing a cell or tissue on the substrate of the multiple electrode.

16. An integrated cell installer comprising a multiple electrode according to claim 4, wherein the integrated cell installer has a cell installing region for placing a cell or tissue on the substrate of the multiple electrode.

17. An integrated cell installer comprising a multiple electrode according to claim 5, wherein the integrated cell installer has a cell installing region for placing a cell or tissue on the substrate of the multiple electrode.

18. An integrated cell installer comprising a multiple electrode according to claim 9, wherein the integrated cell installer has a cell installing region for placing a cell or tissue on the substrate of the multiple electrode.

* * * * *

UNITED STATES PATENT AND TRADEMARK OFFICE
CERTIFICATE OF CORRECTION

PATENT NO. : 7,041,492 B2
APPLICATION NO. : 10/048662
DATED : May 9, 2006
INVENTOR(S) : Hiroaki Oka et al.

It is certified that error appears in the above-identified patent and that said Letters Patent is hereby corrected as shown below:

In claim 3, in column 14, line 51, micro-electrode should be plural, i.e., micro-electrodes.

In claim 4, in column 14, line 51, micro-electrode should be plural, i.e., micro-electrodes.

In claim 5, in column 14, line 52, the first line should read: "A multiple electrode according to claim 1 any of claims 1, . . . .

Signed and Sealed this

Fifteenth Day of August, 2006

JON W. DUDAS
*Director of the United States Patent and Trademark Office*